United States Patent [19]

May et al.

[11] Patent Number: 4,841,156
[45] Date of Patent: Jun. 20, 1989

[54] MEASUREMENT OF THE THICKNESS OF THIN FILMS

[75] Inventors: Joe T. May; Edward A. Casacia, both of Leesburg, Va.

[73] Assignee: Electronic Instrumentation and Technology, Inc., Sterling, Va.

[21] Appl. No.: 49,833

[22] Filed: May 15, 1987

[51] Int. Cl.⁴ ............................................. G01N 21/64
[52] U.S. Cl. .............................. 250/461.1; 250/459.1; 356/381
[58] Field of Search ............... 250/458.1, 459.1, 461.1, 250/461.2; 356/381, 382

[56] References Cited

U.S. PATENT DOCUMENTS

| | | | |
|---|---|---|---|
| 3,854,050 | 12/1974 | Peterson et al. | 250/461.2 |
| 3,956,630 | 5/1976 | Mellows | 250/461.1 |
| 4,055,768 | 10/1977 | Bromberg | 356/317 |
| 4,365,896 | 12/1982 | Mihalow | 356/446 |
| 4,421,772 | 12/1983 | Munck et al. | 250/461.1 |
| 4,516,856 | 5/1985 | Popelka | 250/458.1 |
| 4,622,468 | 11/1986 | Stefanski et al. | 250/458.1 |
| 4,672,209 | 6/1987 | Karasaki et al. | 250/461.1 |
| 4,750,837 | 6/1988 | Gifford et al. | 250/458.1 |

FOREIGN PATENT DOCUMENTS

| | | | |
|---|---|---|---|
| 2907620 | 8/1980 | Fed. Rep. of Germany | 356/436 |
| 57-86743 | 5/1982 | Japan | 250/461.1 |
| 84/00609 | 2/1984 | World Int. Prop. O. | 250/458.1 |

OTHER PUBLICATIONS

A. Smart et al., "Measurement of Thin Liquid Films by a Fluorescence Technique", INSPEC, vol. 29(1), pp. 41–47, 7/74.

Primary Examiner—Carolyn E. Fields
Assistant Examiner—John A. Miller
Attorney, Agent, or Firm—C. Lamont Whitham; Michael E. Whitham

[57] ABSTRACT

An ultraviolet source (14) directs selected ultraviolet radiation onto a thin film (10) to excite it. The thin film fluoresces, either naturally or as a result of adding fluorescing material. The amount of light fluoresced is proportional to the film thickness. An optical filter (16) selectively transmits fluoresced wavelengths, excluding exciting wavelengths. A photodetector (18) converts the light to an electrical signal which is processed by signal processing circuits (20) and displayed on a readout (26). The output is compensated for variations in the intensity of the exciting ultraviolet radiation by generating a second electrical signal (13', 18') proportional to the intensity of the exciting radiation and dividing the first electrical signal by a function of said second electrical signal. The compensated output is then calibrated to assure precision and accurate measurements.

Various materials may be selectively measured, individually in the presence of others by choosing appropriate excitation and emission wavelengths. The amount of fluoresced light is linear with respect to the amount of material present as long as the layer is quite thin. As the layer thickness increases, the amount of light to thickness relationship becomes non-linear.

8 Claims, 2 Drawing Sheets

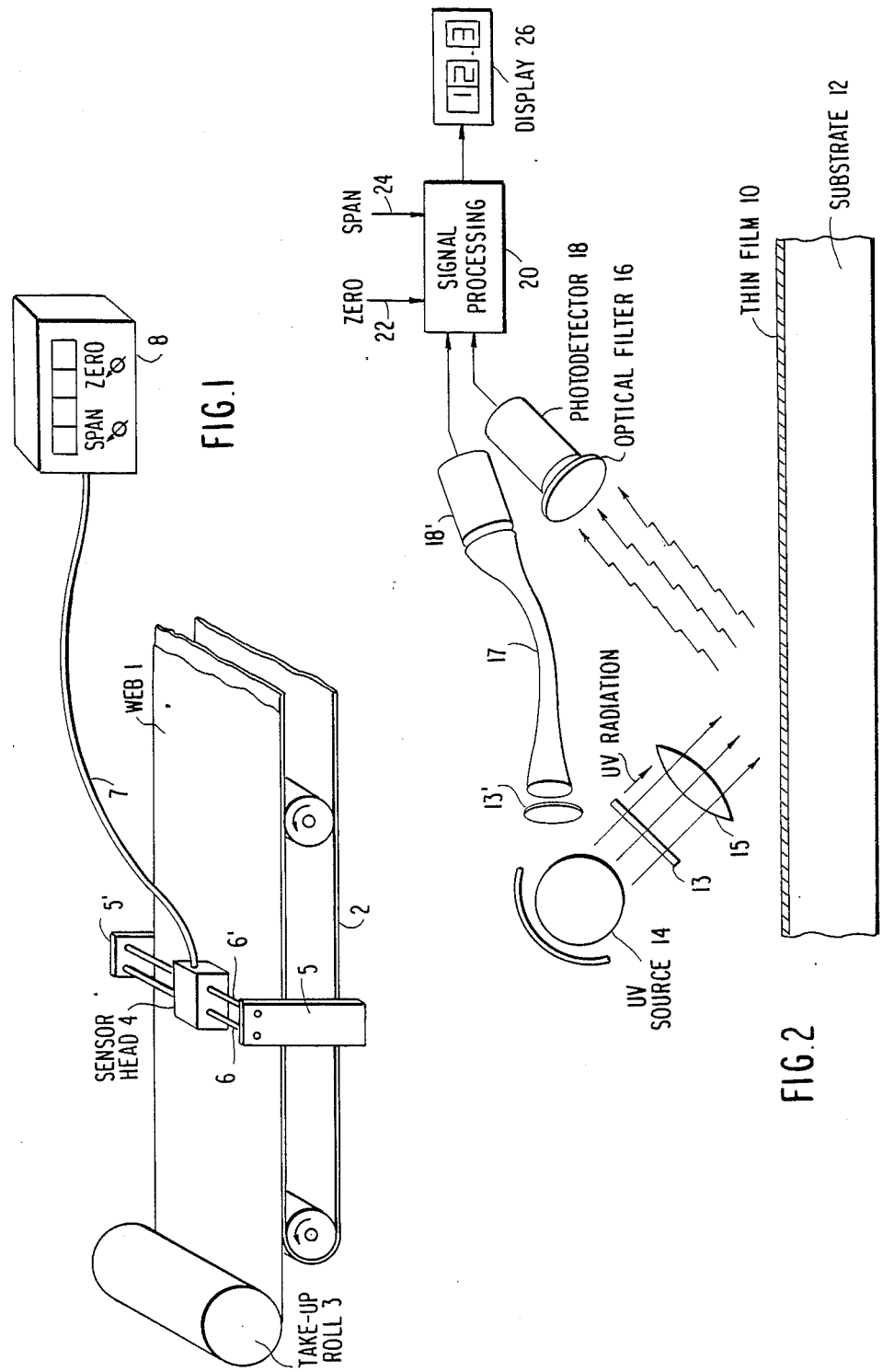

MEASUREMENT OF THE THICKNESS OF THIN FILMS

BACKGROUND OF THE INVENTION

1. Field of the Invention

The present invention generally relates to the measurement of the thickness of thin films and, more particularly, to a new technique of measuring thin film thickness using ultraviolet fluorescense.

2. Description of the Prior Art

Measurement of a thin film on a thick substrate historically has been a difficult problem. An example of such a measurement is the determination of the amount of adhesive on an envelope flap. The adhesive thickness is on the order of 0.0007 inches thick, while the envelope is on the order of 0.005 inches thick. Because the ratio of adhesive to envelope thickness is about 7.1:1, a 10% change in adhesive thickness presents an overall thickness change of only 1.4%. Thus, measuring thickness of the adhesive layer on an envelope using typical mass or absorption techniques, such as beta ray absorption, is difficult because thickness changes in the adhesive produce only small changes in the total measurement. This measurement problem is common to a large number of situations in which a relatively bulky substrate is coated with a thin film or layer of other material or in which it is desired to measure the thickness of a thin film alone.

U.S. Pat. No. 3,395,278 to McDivitt discloses a method of measuring the coating thickness of articles. In the specific example disclosed, coatings on glass containers are measured using a reflectivity device which employs the use of ultraviolet light. To make the glassware scratch resistant, the glassware is provided with a metallo-organic ester which provides a transparent coating on the glassware. The thickness of the coating is measured by measuring the reflectivity of the coating to the untraviolet light.

Other examples of reflectance type thickness measurement techniques are disclosed in U.S. Pat. No. 3,016,464 to Bailey and U.S. Pat. No. 3,325,649 to Bird. As an alternative to reflection type measurements, it is also possible to measure thickness using an inverse transmission or obscuration type of measurement. Examples of this type of measurement are disclosed, for example, in U.S. Pat. No. 2,813,981 to Friedman and U.S. Pat. No. 3,076,723 to Covington.

U.S. Pat. No. 4,296,326 to Haslop et al. discloses a method of detecting watermarks in paper. This measurement is accomplished by an absorption measurement wherein the reflectance of ultraviolet radiation by a sheet of paper in the vicinity of the watermark is measured. Alternatively, the transmittance or the fluorescence of the sheet of paper in the presence of ultraviolet radiation can be measured. The measured value is compared to a reference value obtained by a measurement of the same parameter outside the watermark area.

U.S. Pat. No. 3,577,885 to Wells discloses a method for detecting a coating transfer from a coated film which involves incorporating a fluorescent material in the coating. The coating is applied to one surface of the film and subsequent scanning of the surface of the film with ultraviolet light will allow detection of the fluorescent material to confirm the successful transfer of the coating.

SUMMARY OF THE INVENTION

It is an object of this invention to provide a thin film measuring system wherein various materials in a film may be selectively measured, individually and in the presence of other materials.

It is another object of the present invention to provide a simple and accurate yet highly selective method of measuring the thickness of thin films on thick substrates.

According to the present invention, a technique, based on fluoresence, provides a solution to the problem of measuring the thickness of thin films alone or thin films on thick substrates. An ultraviolet source directs radiation onto the thin film surface to be measured. The thin film fluoresces, either naturally or as a result of adding fluorescing material; i.e., it re-radiates light at a longer wavelength than the incident ultraviolet light which is used to excite the material of the thin film. The excitation wavelengths and the wavelengths of the re-radiated light are uniquely determined by the intrinsic properties of the thin film and/or additive. Optical filters selectively transmit exciting and fluoresced wavelengths. The excitation filter selects only exciting wavelengths of interest, while the emission filter accepts only fluoresced wevelengths of interest. The emission filter excludes both the exciting ultraviolet light and fluoresced light from materials in the thin film not of interest. That is, various materials may be selectively measured, and unwanted materials can be made to "disappear" because they do not fluoresce at the wavelengths passed by the filter.

The amount of light fluoresced is proportional to the film thickness, among other variables. The other variables, including variations in the ultraviolet irradiation intensity, are held constant or compensated for so that the light striking the photodetector is proportional to film thickness. The amount of fluoresced light is linear with respect to the amount of material present as long as the layer is quite thin. As the thickness increases, the amount of light to thickness relationship becomes non-linear and ultimately the amount of light fails to increase because of blocking within the film itself. Up to a certain thickness, the non-linear function can be linearized if necessary.

The photodetector converts the light to an electrical signal which is processed and displayed. A "ZERO" control allows establishment of a zero reading in the absence of any film on the substrate. A "SPAN" control provides the ability to place a sample with known film thickness under the ultraviolet source and, by adjusting the "SPAN" control, the system can be calibrated directly in engineering units, such as grams per meter$^2$. A digital display provides direct numerical readout. Other display means, such as an analog meter, a strip chart recorder or a video display, may also be used.

BRIEF DESCRIPTION OF THE DRAWINGS

The foregoing and other objects, aspects and advantages of the invention will be better understood from the following detailed description of the invention with reference to the drawings, in which:

FIG. 1 is a pictorial diagram showing a typical application of the invention for measuring the thickness of a thin film on a moving web of material;

FIG. 2 is a block diagram illustrating the basic measuring technique and sysytem according to the present invention.

DETAILED DESCRIPTION OF THE PREFERRED EMBODIMENT OF THE INVENTION

Figure 3:
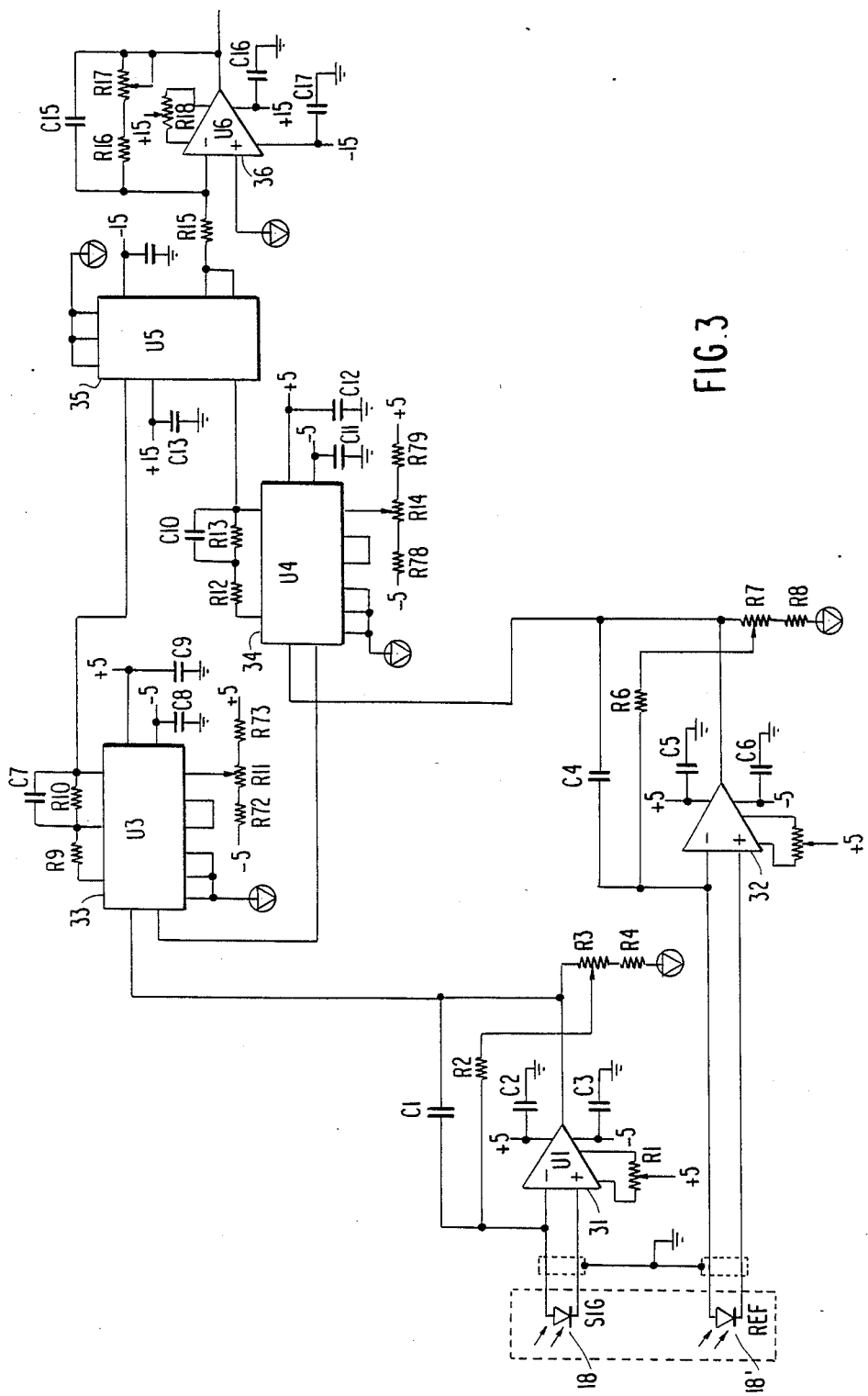
FIG. 3 is a detailed block and schematic diagram of the signal processing circuitry of the system shown in FIG. 2 according to a preferred embodiment of the invention.

Referring now to the drawings, and more particularly to FIG. 1, there is shown a typical application of the thin film measuring system according to the invention. In FIG. 1, a web of material 1 in the form of a thin film, such as a thin film of polyester, is transported on a conveyor 2 from a coating station (not shown) to a take up roll 3. Alternatively, the web 1 may be a substrate which is itself coated with a thin film of, for example, polyester, urethane or cyanoacrylate or other material for purposes of protecting the surface of the web or to provide the surface of the web with some desired characteristic, such as making it impervious to water. A sensor head 4 is supported over the moving web by vertical support brackets 5 and 5' on either side of the conveyor 2 and horizontal guides 6 and 6' which are journaled to the upper ends of brackets 5 and 5'. The sensor head 4 may be, for example, servo controlled to be positioned at any location from edge to edge of the web 1 transverse to the motion of the web. The output from the sensor head 4 is connected by a cable 7 to the measuring and display unit 8. This unit is provided with only two basic controls, a "ZERO" adjustment and a "SPAN" adjustment. These will be described in more detail hereinafter, but briefly described, the "ZERO" adjustment is made initially by placing a sample of material with no film or coating under the sensor head 4 and adjusting the readout to zero. Then, a sample of material with a film of known thickness is placed under the sensor head, and the "SPAN" adjustment is made to cause a readout equal to the known thickness.

This basic system, while but one example of an application of the invention, can be modified or elaborated on depending on specific requirements. For example, if the film on web 1 is a composite of more than one component and it is desired to measure the thicknesses of each component, this can be done with a multi-channel system wherein the sensor head 4 is replicated two, three or more times, each on a common support or on separate and independent supports. The manner in which the several sensor heads and the measuring circuitry are effective in differentiating between the several components of the thin film will be made clear in the description to follow. In addition, it is possible to the use the output of the measuring unit to control the coating station so that a precise and controlled thin film is applied to the web.

FIG. 2 shows in general block diagram form the basic thin film measurement technique using fluorescence according to the invention. The thin film 10 to be measured is supported or adhered to a substrate 12, which may itself be a thick film, a web or the like. Alternatively, the thickness of a thin film unsupported by a substrate may be measured. An ultraviolet source 14 is positioned to direct ultraviolet radiation onto the thin film 10. The ultraviolet radiation is filtered as generally indicated by the filter 13 and focussed as generally indicated by the lens 15. The wavelength of the exciting ultraviolet radiation is carefully controlled by selecting the filter 13 depending on the material of the thin film. The ultraviolet light is focussed by the lens 15 to impinge on either a small, selective sample of the film or a larger area of the film depending on the type and purpose of the measurement to be made. The lens 15 may be either fixed focus or variable focus, again depending on the specific application.

The ultraviolet radiation causes the material of the thin film or material added to the film material before it is applied to the substrate 12 to become excited. That is, electrons are raised to higher energy levels. Subsequently, the electrons drop to a lower energy level emitting photons having wavelengths longer than the wavelength of the exciting radiation. As a specific example, the exciting ultraviolet radiation may have a wavelength of 365 nm and the emitted or fluorescent wavelength may have a wavelength of 445 nm.

The fluoresced light is filtered by an optical filter 16 which selectively transmits light of a desired wavelength to the photodector 18. A filter 13' having the same characteristics as filter 13 is positioned adjacent the ultraviolet source 14 at the entrance to a fiber optic cable 17. The other end of the fiber optic cable is positioned adjacent a second photodetector 18'. The photodetectors 18 and 18' convert the light received by each to respective electrical signals which are supplied to signal processing circuits 20. The signal processing circuits 20 amplify the electrical signals from the photodetectors 18 and 18' and then divide the two signals so that the relative value of the signal detected by photodetector 18 is a function of the light detected by the photodetector 18'. This assures that the measurement of the signal from photodetector 18 is calibrated to or compensated for the variations in intensity of the exciting radiation. The signal processing circuits measure the absolute signal level of the thus compensated signal to determine the amount of fluoresced light from the thin film 10. In order to make this measurement with precision and accuracy, the signal processing circuits 20 are provided with a "ZERO" control 22 and a "SPAN" control 24. The "ZERO" control 22 allows establishment of a zero reading in the absence of any film on the substrate. The "SPAN" control 24 provides the ability to place a sample with known film thickness under the ultraviolet source 14 and, by adjusting the "SPAN" control 24, the system can be calibrated.

Once the basic measurement has been accomplished by the signal processing circuits 20, an output must be generated to allow the user of the system to have the benefit of the measurement. This is accomplished by any of several ways. For example, the output of the signal processing circuits can be connected directly to an analog meter to provide a direct readout of the measured thickness. The scale of the meter movement would in this case be calibrated in the desired units of measurement. Alternatively, the output of the signal processing circuits can be connected to a strip chart recorder or an oscilloscope. In the preferred embodiment, an analog-to-digital converter which may be part of the signal processing circuits 20 or a digital display converts the analog output from the signal processing circuits to a digital value, and this digital value is used to drive a digital readout or display 26. In the course of making the "SPAN" control adjustment, the system can be calibrated to provide a readout directly in engineering units.

FIG. 3 shows in more detail the signal processing ciruits. Photodetectors 18 and 18' are connected respectively to the inputs of operational amplifiers 31 and 32, the purpose of which is to convert the current signals from the photodetectors to amplified voltage signals. The outputs of amplifiers 31 and 32 are connected to respective low pass filters 33 and 34. These low pass filters may be implemented with type MF-6 integrated circuits (ICs) manufactured by National Semiconductor of Santa Clara, Calif. The outputs of the low pass filters 33 and 34 are signals which are respectively proportional to the intensity of the fluoresced light from the thin film being measured and the exciting radiation from the ultraviolet source 14. These two signals are supplied to the inputs of a divider 35 which takes a ratio of the output of low pass filter 33 to the output of low pass filter 34; i.e., the level of the light detected by photodetector 18 to the level of light detected by photodetector 18' multiplied by a predetermined constant factor. This eliminates any variation in the amount of fluoresced light due to a variation in the intensity of the exciting radiation so that the amount of fluoresced light is primarily a function of the thickness of component of the thin film selected to be measured by the optical filters. The divider 35 may be implemented with an AD534JH type IC manufactured by Analog Devices of Norwood, Mass.

The output of the divider 35 is therefore a signal which is compensated for any variation in the exciting radiation impinging on the thin film. This compensated signal is then calibrated in the last stage of the signal processing circuits which comprises operational amplifier 36. Amplifier 36 is provided with a negative feedback circuit which includes a potentiometer R17 and also with a level adjust potentiometer R18. The latter is the "ZERO" adjust potentiometer, while the former is the "SPAN" adjust potentiometer. Initially, a sample with no film is placed under the sensor head, and potentiometer R18 is adjusted so that the output from amplifier 36 is zero or null. Then, a sample with a film of known thickness is placed under the sensor head, and potentiometer R17 is adjusted so that the output from amplifier 36, as read by the display 26, is equal to the value of the thickness of the sample. In this manner, the output is calibrated to provide precision and accurate measurements. This calibrated output may be provided to any desired display or even used as a control signal to control a coating apparatus, for example.

Specific examples of excitation and emission wavelengths for several materials are as follows:

|  | Excitation | Emission |
| --- | --- | --- |
| a. Polyester | 265-270 nm | 290-300 nm |
| b. Polyester | 340-350 nm | 380-400 nm |
| c. Urethane | 360-370 nm | 420-460 nm |
| d. Cyanoacrylate | 310-320 nm | 340-350 nm |

The foregoing are given by way of example only and are not necessarily the only usable combinations. In those applications which may require it, the following fluorescing agents may be added to the material of the thin film:

UVITEX TM —A material sold commercially by Ceiby-Geigy to absorb ultraviolet radiation in the range of 340-360 nm and fluoresces blue light in the range of 420-480 nm.

Quinine Sulfate—A chemical which absorbs ultraviolet radiation in the 370-390 nm region and emits strongly in the 440-450 nm region. These are but two examples of fluorescing compounds which may be used in the practice of the invention.

Fluorescers are used to permit measurement of a coating thickness in the situation where the coating fluoresces at the same wavelengths as the film. For example, polyethylene and certain acrylic based adhesives both fluoresce strongly at 375-390 nm when irradiated at 345 nm. Addition of a fixed amount of UVITEX TM fluorescer to the acrylic only produces a fluorescence at 440 nm which is proportional to the amount of acrylic adhesive present.

Although the disclosed technique has broad application, each situation must be considered individually. Differences in fluorescence characteristics, sensitivity of the materials to ultraviolet radiation, ambient conditions and the like may require different excitation, filtering, detection and compensation. However, the analysis required is not difficult and the technique holds substantial promise in a large number of widely differing applications. Therefore, while the invention has been described in terms of a single preferred embodiment, those skilled in the art will recognize that the invention may be practiced with modification without departing from the spirit and scope of the appended claims.

Having thus described our invention, what we claim as new and desire to secure by Letters Patent is as follows:

1. A method of selectively measuring the thickness of a film or a film on a substrate comprising the steps of:
exciting the film with ultraviolet radiation of first wavelengths selected based on the florescence characteristics of the material of the film to cause the film to fluoresce by emitting light of a longer ultraviolet wavelength than the exciting radiation;
detecting the ultraviolet radiation of said first selected wavelengths to produce a first electrical signal proportional to an instantaneous intensity of said ultraviolet radiation of said first selected wavelengths;
filtering and detecting the emitted light from the film to produce a second electrical signal proportional to second selected wavelengths of the emitted light;
dividing said second electrical signal by said first electrical signal to produce an instantaneous quotient output calibrated to the intensity of the exciting radiation and which is a direct measurement of the thickness of the film; and
displaying the calibrated output.

2. The method of claim 1 further comprising the step of filtering the ultraviolet radiation of the exciting radiation so that the film is excited only by said first selected wavelengths of ultraviolet radiation.

3. The method of claim 1 wherein the calibrated output is further produced by the step of multiplying said quotient by a predetermined constant 4. The method of claim 1 further comprising the step of adding a fluorescing agent to the film and wheein the emitted light which is filtered and detected is produced by said fluorescing agent.

5. A system for selectively measuring the thickness of a film or a film on a substrate comprising:
a source of ultraviolet radiation positioned to direct ultraviolet radiation of first wavelengths selected based on the florescence characteristics of the material of the film onto said film, said film being excited by the ultraviolet radiation to fluoresce by emitting ultraviolet light of a longer wavelength than the exciting wavelength;

first detecting means for receiving light from said source of ultraviolet radiation and producing a first electrical signal proportional to an instantaneous intensity of said ultraviolet radiation of said first selected wavelengths;

filtering and second detecting means positioned adjacent said film for filtering the emitted light and producing a second electrical signal proportional to second selected wavelengths of the emitted light;

dividing means connected to receive said first and second electrical signals for producing an instantaneous quotient output calibrated to the intensity of the exciting radiation and which is a direct measurement of the thickness of said film; and means for displaying said calibrated output.

6. The system recited in claim 5 wherein said first detecting means and said filtering and second detecting means comprises:

first and second optical filters, said first optical filter being positioned to receive radiation directly from said source of ultraviolet radiation and pass only said first selected wavelengths and said second optical filter being positioned to receive emitted light from said film and pass only said second selected wavelengths; and first and second photodetectors positioned to receive light passed by said first and second filters, respectively, said first photodetector producing a first electrical signal proportional to the intensity of the ultraviolet radiation of said first selected wavelengths and said second photodecter producing a second electrical signal proportional to the intensity of the emitted light of said second selected wavelengths.

7. The system recited in claim 6 further comprising:

first and second amplifying means connected to receive said first and second electrical signals, respectively, for producing first and second amplified outputs;

said dividing means being connected to receive said first and second amplified outputs for generating a compensated output proportional to the quotient of said second amplified output divided by a function of said first amplified output; and zero adjust and span control means responsive to said compensated output for adjusting said compensated output to the absence of a film and to a known film thickness, respectively.

8. The system as recited in claim 7 wherein said means for displaying comprises a numerical display means for providing a digital disolay of said calibrated output.

* * * * *